United States Patent
Mariller

(10) Patent No.: US 12,420,061 B2
(45) Date of Patent: Sep. 23, 2025

(54) MEDICAL INSTRUMENT WITH INJECTION NEEDLES

(71) Applicant: DOC-INVENT SA, Lausanne (CH)

(72) Inventor: Alain Mariller, Les Monts-de-Corsier (CH)

(73) Assignee: DOC-INVENT SA, Lausanne (CH)

( * ) Notice: Subject to any disclaimer, the term of this patent is extended or adjusted under 35 U.S.C. 154(b) by 672 days.

(21) Appl. No.: 17/440,556

(22) PCT Filed: Mar. 19, 2020

(86) PCT No.: PCT/IB2020/052495
§ 371 (c)(1),
(2) Date: Sep. 17, 2021

(87) PCT Pub. No.: WO2020/188508
PCT Pub. Date: Sep. 24, 2020

(65) Prior Publication Data
US 2022/0143364 A1      May 12, 2022

(30) Foreign Application Priority Data
Mar. 20, 2019   (CH) .................... 00357/19

(51) Int. Cl.
*A61M 25/00*          (2006.01)
(52) U.S. Cl.
CPC . *A61M 25/0084* (2013.01); *A61M 2025/0087* (2013.01)
(58) Field of Classification Search
CPC ...... A61M 25/0084; A61M 2025/0085; A61M 2025/0086; A61M 2025/0087; A61M 2025/0089; A61M 2025/009; A61M 2025/0092; A61M 2025/0093; A61M 2025/0095; A61M 2025/0096
See application file for complete search history.

(56) References Cited

U.S. PATENT DOCUMENTS

| | | |
|---|---|---|
| 5,419,777 A | 5/1995 | Hofling |
| 5,538,504 A | 7/1996 | Linden et al. |
| 6,258,064 B1 | 7/2001 | Smith et al. |
| 6,302,870 B1 * | 10/2001 | Jacobsen ............... A61B 17/22 604/170.03 |
| 6,585,694 B1 | 7/2003 | Smith et al. |
| 6,629,987 B1 | 10/2003 | Gambale et al. |
| 2002/0049414 A1 | 4/2002 | Nobles et al. |

(Continued)

FOREIGN PATENT DOCUMENTS

| | | |
|---|---|---|
| WO | 92/10142 | 6/1992 |
| WO | 01/08741 | 2/2001 |

OTHER PUBLICATIONS

International Search Report for PCT/IB2020/052495, mailed Jun. 23, 2020, 6 pages.

(Continued)

*Primary Examiner* — Kami A Bosworth
(74) *Attorney, Agent, or Firm* — NIXON & VANDERHYE

(57) ABSTRACT

The invention concerns an instrument, for a medical application, said instrument comprising a body (1), at least one needle, channel means (15) to bring a fluid to said at least one needle, and actuating means (6) for moving said at least one needle from a retracted position to an extended position by rotation of actuating means (6) with respect to the body.

12 Claims, 4 Drawing Sheets

(56) References Cited

U.S. PATENT DOCUMENTS

| | | | |
|---|---|---|---|
| 2002/0143302 A1* | 10/2002 | Hinchliffe | A61B 18/00 |
| | | | 604/95.01 |
| 2004/0138621 A1 | 7/2004 | Jahns et al. | |
| 2009/0112161 A1 | 4/2009 | Maerten et al. | |
| 2012/0071832 A1 | 3/2012 | Bunch | |
| 2013/0053792 A1* | 2/2013 | Fischell | A61M 25/0662 |
| | | | 604/275 |
| 2015/0005740 A1* | 1/2015 | Foster | A61M 5/158 |
| | | | 604/95.01 |
| 2017/0232229 A1* | 8/2017 | Flores | A61M 25/0097 |
| | | | 604/506 |

OTHER PUBLICATIONS

Written Opinion of the ISA for PCT/IB2020/052495, mailed Jun. 23, 2020, 7 pages.

* cited by examiner

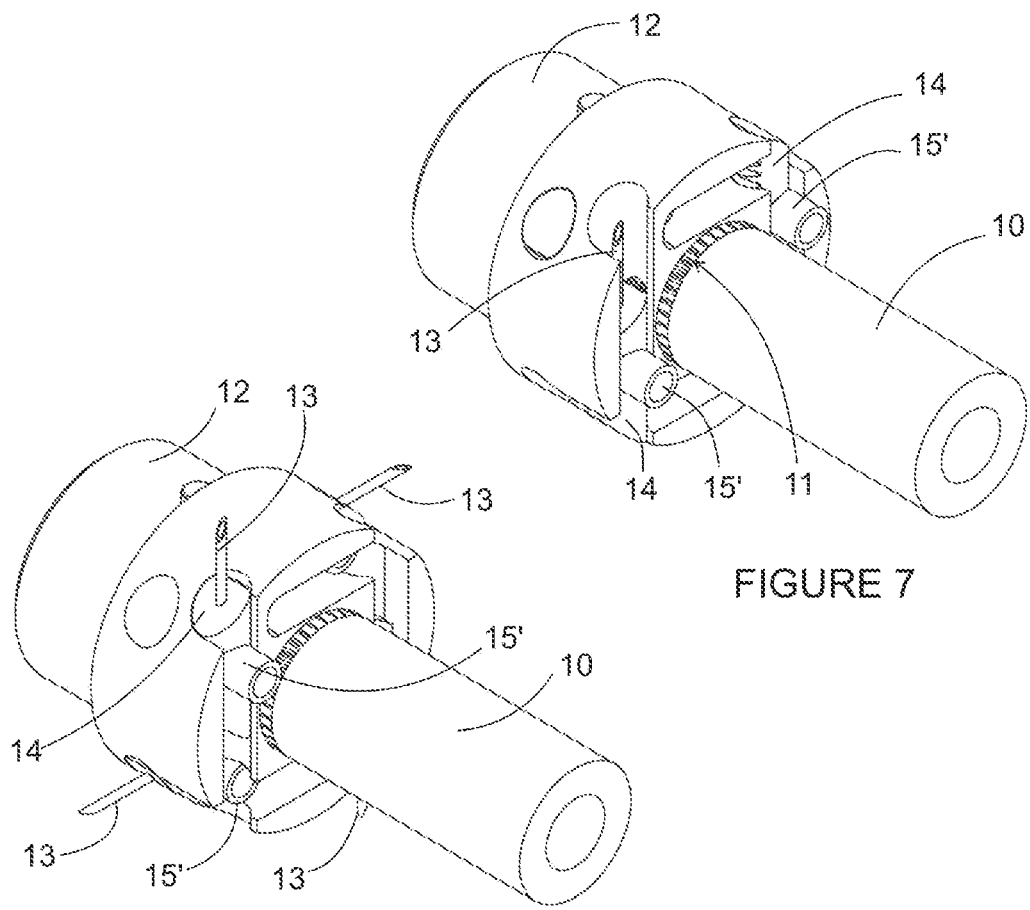
FIGURE 7
FIGURE 8
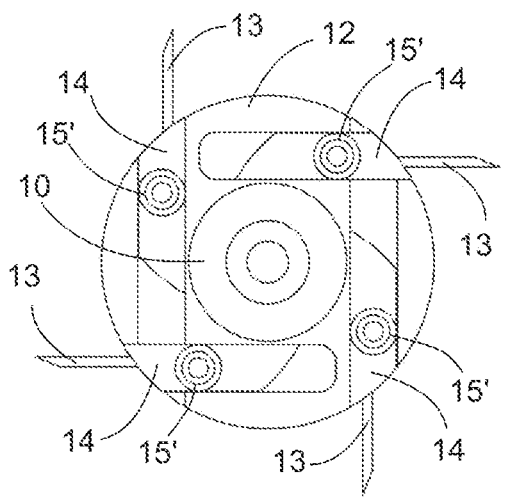
FIGURE 9
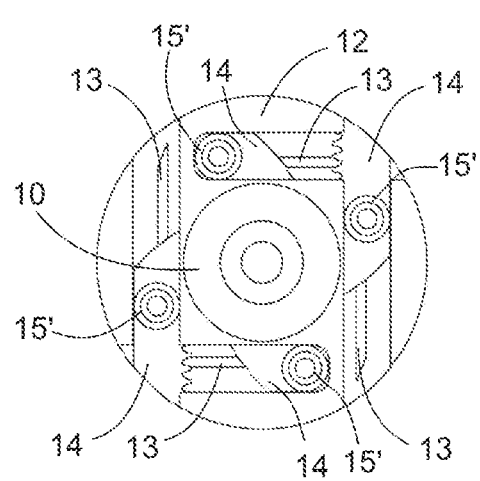
FIGURE 10

MEDICAL INSTRUMENT WITH INJECTION NEEDLES

CORRESPONDING APPLICATION

The present patent application is the U.S. national phase of International Application No. PCT/IB2020/052495 filed on Mar. 19, 2020, that designated the United States, and claims priority to CH Patent Application No. 00357/19 filed on Mar. 20, 2019, the entire contents of each of which are hereby incorporated by reference.

TECHNICAL FIELD

The present invention relates to a medical instrument comprising a tubular body housing at least one injection needle.

BACKGROUND ART

A medical instrument of this type in the form of a catheter is known for example from U.S. Pat. No. 5,538,504. This catheter has a tubular body housing one injection needle with a radially outwardly directed tip portion in an axially undisplaceable manner, and has a control element for deploying the tip of the injection needle out sideways from the tubular body.

A tubular body of the catheter houses inside said body an injection needle which has a radially outwardly directed tip portion. In the tubular body there is a corresponding opening, via which at least the tip of the outwardly directed tip portion can pass through radially outwards. Provided in the region of the outwardly directed tip portion is a control element, by means of which the tip portion can be pressed radially outwards as and when required.

Without actuation of the control element, the outwardly directed tip portion is fully retracted in the tubular body. In this state, the catheter can be pushed into a vessel, for example into a urethra, or another opening or cavity.

The control element comprises an inflatable balloon, which is situated in the catheter directly alongside the outwardly directed tip portion. If the balloon is inflated, whether by means of a liquid or a pressurized gas, the inflated balloon presses the tip portion radially outwards, so that at least the tip moves radially outwards beyond the outer side of the tubular body and punctures the vessel. A medicament can then be administered.

After application, the liquid or the pressurized gas is let out again, so that the balloon can contract. The return of the outwardly directed tip portion then takes place on the basis of the elasticity of the outwardly directed tip portion, which usually consists of metallic material. A disadvantage of this is that it cannot be ensured with absolute certainty that the outwardly directed tip portion will move back again completely into the tubular body.

This is because the tip has punctured the tissue of the vessel and is held relatively firmly there in the puncture position.

This can have fatal consequences when the medical instrument is withdrawn from the vessel, to be specific that the vessel may be damaged, or even lacerated, by the tip still protruding beyond the outer side of the tubular body over the entire length over which it is withdrawn.

From WO 92/10142 it is known to move a number of injection needles out of a tubular body in a circumferentially distributed manner, so that in the case of a relatively large vessel it can be supplied with a medicament at multiple locations circumferentially. Here, the deployment and retraction are controlled by an axial longitudinal displacement of the injection needles. Provided for this purpose in the tubular body is a control element with recessed channels, in which the injection needles can be moved axially back and forth. In the region of the lateral outlets, these channels have outwardly directed curvatures, over which the injection needles then emerge from the tubular body in an outwardly directed manner.

A disadvantage of this structural design is that the injection needles must be axially displaced back and forth in the tubular body, which is problematic in the case of extremely thin injection needles and can lead to them becoming caught or stuck or even damaged (for example bent). Considerable design measures have to be taken here to make sure that, before the medical instrument is withdrawn, it is ensured that all the injection needles are fully retracted again in the device and do not risk injuring the patient.

Another example of a prior art is given in US 2009/0112161. This publication discloses a medical instrument comprising a tubular body housing at least one injection needle with a radially outwardly directed tip portion in an axially undisplaceable manner. A control element serves for deploying the tip of the injection needle out sideways from the tubular body. It is proposed that the control element is housed in the tubular body in an axially displaceable manner, and that said element it in operative connection with the at least one injection needle in such a way that, in a first axially displaced position, the outwardly directed tip portion of the injection needle is fully retracted in the body and, in a second axially displaced position, at least the tip of the outwardly directed tip portion is pressed sideways out from the tubular body.

SUMMARY OF THE INVENTION

The intended area of use of the present invention is mainly as an anuscope, i.e. the tubular body is of a considerable length and a considerable diameter and serves the purpose of applying a medicament in a circumferentially distributed manner in the anal canal. Of course, the present invention is not limited to this single application and others are possible as well with a suitable adaption of the size and shape of the device using the principles of the present invention.

In any case, whatever the application or use, if tips of injection needles were still to protrude radially beyond the tubular body surface when the instrument is withdrawn from the anus, or from another body cavity in which the instrument has been inserted, considerable injuries would occur for the patient and they must be avoided.

It is therefore an object of the present invention to improve the devices and medical instruments known in the art.

It is a further aim of the present invention to develop a medical instrument of the above-mentioned type in that the outwardly directed tip portions of the injection needles are moved in a defined manner into the deployed position, and back into a fully retracted position in a safe and efficient manner.

In embodiments the invention concerns an instrument, for example for a medical application, the instrument comprising a body, at least one needle, channel means connected to said at least one needle to bring a fluid to said at least one needle, actuating means comprising an actuator for moving said at least one needle from a retracted position in said body to an extended position protruding from said body by a rotation of said actuator with respect to the body.

In embodiments the movement of the at least one needle from the retracted position to the extended position is rectilinear. In other embodiments, the movement may not be rectilinear, for example incurved or rotational for example.

In embodiments the actuating means comprise teeth cooperating together.

In embodiments the actuating means comprise a first set of teeth and each of said needles comprises a second set of teeth.

In embodiments the actuator comprises a shaft with the said first set of teeth.

In embodiments the tooth pitch of the sets of teeth is constant or not. This allows to move the needles according to the same rule (when the pitch is constant) or a different rule (when the pitch is not constant) so that some needles are deployed before others.

In embodiments the instrument comprises at least three needles.

In embodiments the channels are flexible.

In embodiments the instrument comprises locking means to lock the position of the actuating element in at least two different positions.

In embodiments the invention concerns a method of using an instrument as defined in the present application, wherein said method comprises the steps of
inserting said instrument in a cavity,
injecting a fluid outside said instrument.

In embodiments the injection step is made through openings of the instrument.

In embodiments the injection step is made through needles protruding from the instrument.

In embodiments after the insertion of the instrument, the needles are deployed before the injection.

Further aims and results achieved by the present invention will be understood from the following description of embodiments therefrom.

BRIEF DESCRIPTION OF THE DRAWINGS

FIGS. 7 to 10 illustrate another detail of an embodiment of the present invention in two positions, FIGS. 7 and 8 in perspective views, FIGS. 9 and 10 in front views.

DETAILED DESCRIPTION

Figure 1:
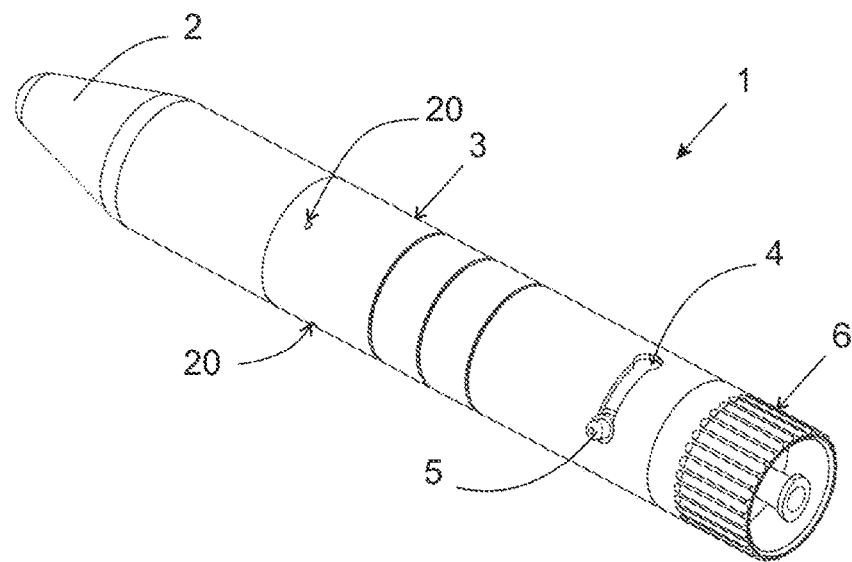
FIG. 1 shows a general perspective view of an instrument according to an embodiment of the present invention viewed from the proximal side of the instrument.

A first perspective view of an instrument according to an embodiment of the present invention is illustrated in FIG. 1, seen in perspective view from the proximal side (i.e. the side of the person (for example surgeon) who is manipulating the instrument).

The instrument comprises a tubular shaped body 1 whose size and shape suit the intended use, for example as an anuscope. Of course, it is possible that for a given use, instruments with different sizes and shapes may be proposed for adaptation to the body of the patient being treated. Accordingly, the shapes and sizes illustrated in the present application are only given as example and should not be construed as limiting the scope of the present invention and application in this respect.

The instrument body 1 comprises a distal end 2, preferably shaped to ease its insertion into a body cavity, a main body part 3, locking means with a locking slit 4 and a locking button 5 and an actuator 6 which will be detailed in the following description.

As illustrated in FIG. 1, the slit 4 preferably comprises two rounded ends which allow the button 5 to be blocked at either ends and thus provide two different locked positions for the instrument as will be explained later herein. The slit may comprise additional rounded positions between the two end positions illustrated to provide intermediate locked positions as well.

Figure 2:
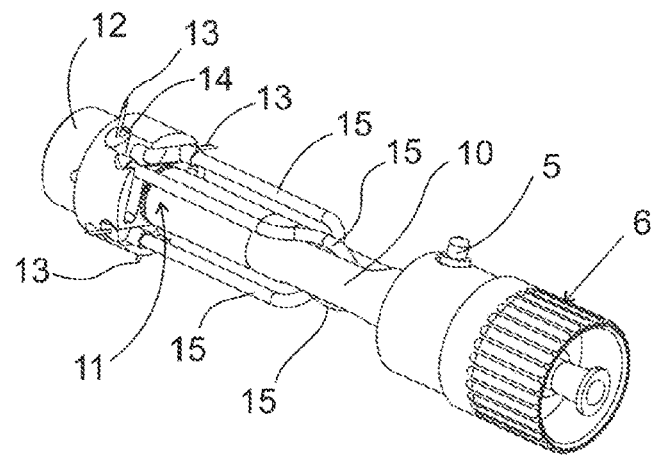
FIG. 2 illustrates a perspective view of a part of an instrument according to an embodiment of the present invention viewed from the proximal side.
Figure 3:
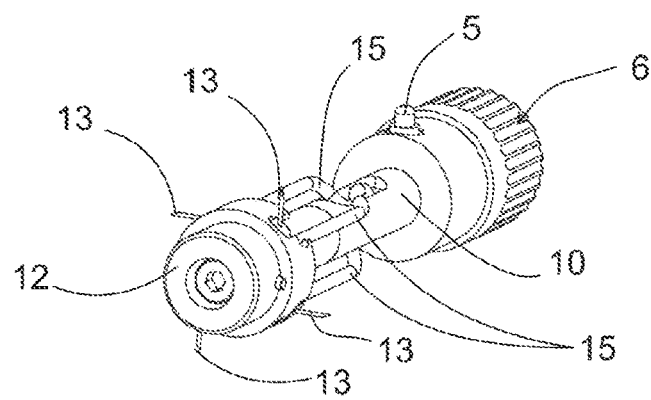
FIG. 3 illustrates a perspective view of a part of an instrument according to an embodiment of the present invention viewed from the distal side.

FIGS. 2 and 3 illustrate several inner parts of the instrument 1 which are used to bring a fluid as is explained now. The instrument 1 thus comprises the actuator 6 with a shaft 10, the distal end of the shaft comprising a teething 11 around its diameter. There is in addition a distal carrier 12 that carries movable needles 13 (for example four needles 13) which are mounted on a respective support 14 with teeth 14' cooperating with the teeth 11 of the shaft 10. The needles 13 are preferably evenly distributed around the carrier 12.

Also illustrated in FIGS. 2 and 3 are channels 15, each needle 13 being preferably connected to a channel 15 via its support 14, said supports 14 allowing a fluidic connection between the channels 15 and the needles 13, thus allowing a delivery by the needles 13 of a fluid present in the channels 15. The channels 15 are preferably non-rigid and are intended to deliver a liquid to the needles 13 when needed, for example by injection. In embodiments, a single channel 15 may be connected to a plurality of needles 13 (for example two or more) and in embodiments, some needles 13 may not be connected to a channel 15. Also the needles may be used to inject a same product or a different product.

Figure 4:
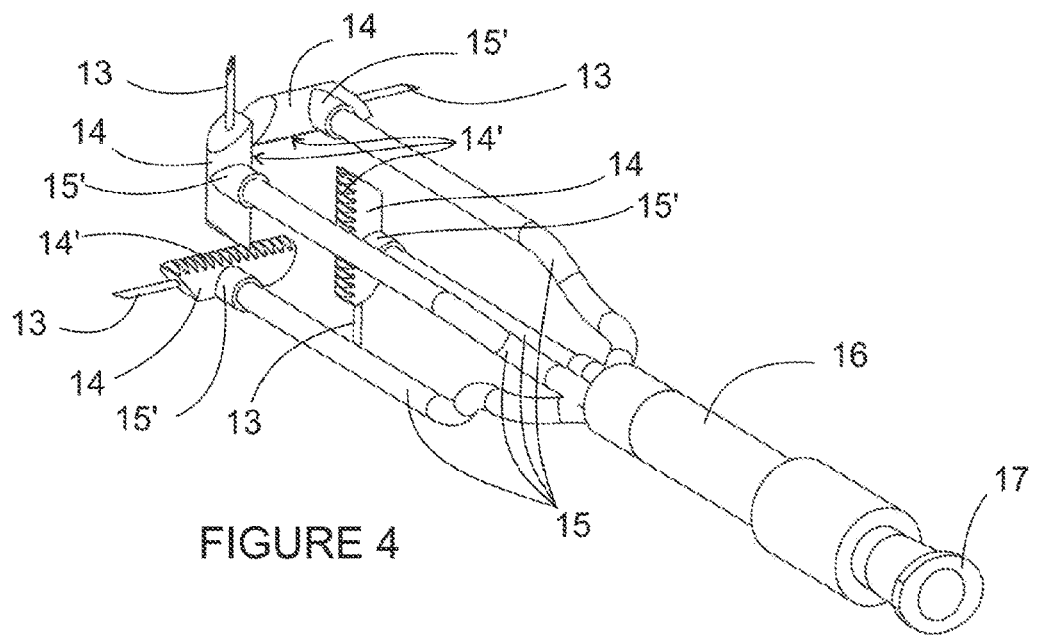
FIG. 4 illustrates a perspective view of another part of an instrument according to an embodiment of the present invention viewed from the proximal side.
Figure 5:
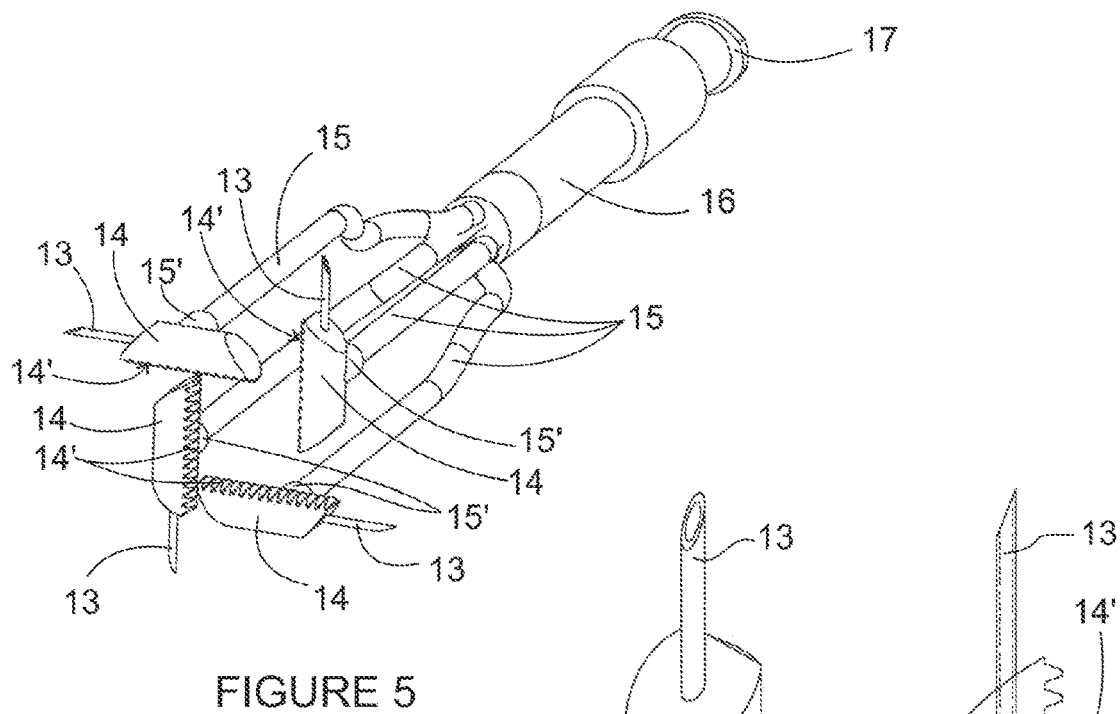
FIG. 5 illustrates a perspective view of another part of an instrument according to an embodiment of the present invention viewed from the distal side.
Figure 6:
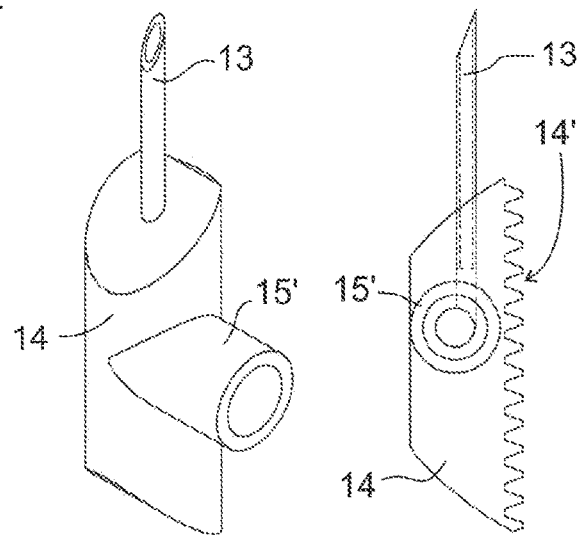
FIG. 6 illustrates details of an embodiment of the present invention.

FIGS. 4 to 6 illustrate in more detail the injection system of the instrument 1. Each needle 13 is mounted on a support 14, each support 14 comprising teeth 14' for cooperation with the teeth 11 of the shaft 10 (see FIGS. 7 and 8). The injection system further comprises a central channel 16 to which the individual channels 15 are connected and the central channel 16 comprises a connecting part 17 for connection to a fluid supply source. The fluid may be any medication necessary for the intended use of the instrument, such as botulinum toxin to treat anal fissures or bulking agents to treat anal incontinence. These are of course non-limiting examples and other products may be envisaged for use with the instrument according to the invention. Also, other types of products may be envisaged with no restriction to a liquid a fluid: for example gas, jelly and other similar products are possible in the frame of the present invention, also depending for example on the intended use of the instrument.

The tooth pitch may be the same for each needle 13 or not, allowing for example to deploy a certain needle or certain needles first and then other needles in a subsequent step. In embodiments, this means that it is also possible to avoid deploying all needles of the instrument.

FIG. 6 is a detail of the needles 13 with their support 14 with teeth 14' and the connecting means 15' for connection to the channel 15 to allow the fluid being transported in the channels 15 to be delivered by the needles 13.

FIGS. 7 to 10 illustrates the principle of functioning of the instrument 1 with the needles 13 in a retracted position for insertion of the instrument (FIGS. 7 and 10) in a cavity and the needles in an extended position (FIGS. 8 and 9) when a fluid is to be delivered in the body of the patient being treated.

The carrier 12 is mounted fixed in the instrument body 1 while the actuator 6 may be rotated with respect to the body 1, for example by gripping its proximal end and turning it to the right (clockwise in FIG. 1). This is allowed by pressing the button 5 so that the locking means are disengaged (FIG. 1).

Turning back to FIGS. 7 and 8, as the carrier 12 is fixed with respect to the actuator 6, a relative rotation of the actuator 6 will also rotate shaft 10 which carry teeth 11 relatively to carrier 12. The carrier 12 carries the needles 13 with their supports 14, the teeth 14' of the supports being engaged in the teeth 11 of the shaft. The rotation of the shaft 10 will then have the effect of moving the needles 13 and their support 14 in translation in the carrier 12. This can be understood by comparing the situation of FIGS. 7 and 8, FIG. 7 showing the needles 13 retracted and FIG. 8 the needles extended or deployed. This is achieved for example by a rotation of the shaft to the right (clockwise) with respect to the carrier 12.

The inverse movement of the shaft (to the left in FIG. 8, i.e. counterclockwise) will have the effect of retracting the needles 13 and their supports 14, to reach the position of FIG. 7.

FIG. 9 shows the same position as in FIG. 8, and FIG. 10 the same position as in FIG. 7, in front views, the change of position of the needles (deployed or retracted) being carried out by a relative rotation of the shaft 10 with respect to the carrier 12. As one can see, the movement of the needles is perpendicular to the axis of the device which makes the system more reliable and with a better penetration of the needles in the area to be treated by the instrument.

Figure 11:
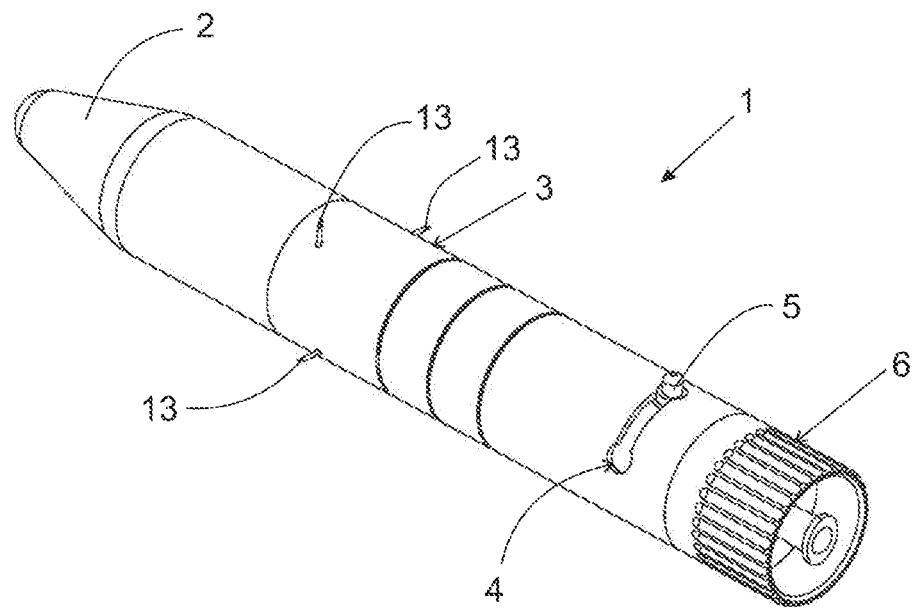
FIG. 11 illustrates the same view as FIG. 1 but with an instrument in a second position.

Turning back to FIG. 1, the references 20 identify openings in the body 1 through which the needles 13 will protrude when in extended positions as in FIG. 8 or 9, this being shown on FIG. 11.

Specifically, FIG. 11 illustrates the same view as FIG. 1 but with an instrument in a second position, that is with the needles 13 protruding from the instrument. As one can remark in this figure, the locking button 5 is at another end of the locking slit 4 compared to FIG. 1, indicating a rotation of the actuator 6.

Figure 12:
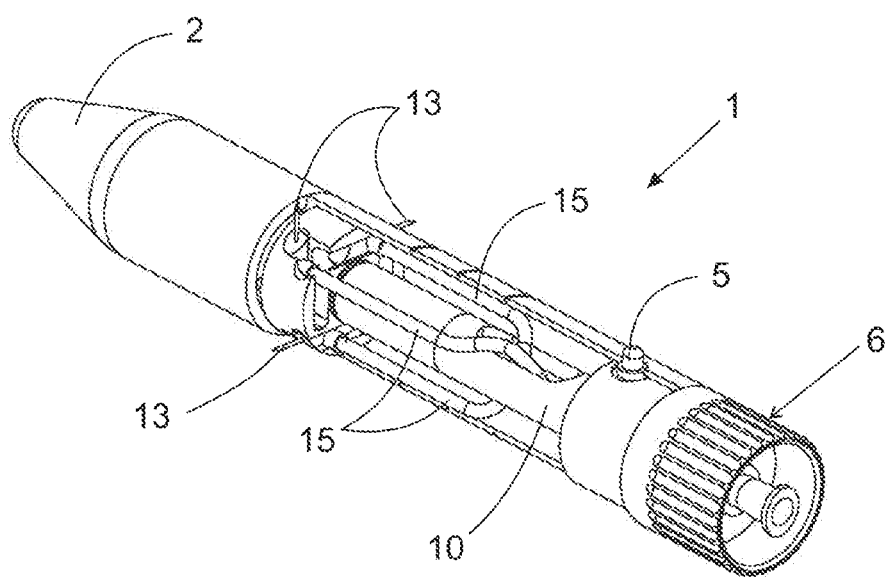
FIG. 12 illustrates a general perspective view of an instrument according to an embodiment of the present invention viewed from the proximal side of the instrument with an open part showing the inner arrangements of elements of the instrument.

FIG. 12 illustrates a general perspective view of an instrument according to an embodiment of the present invention viewed from the proximal side of the instrument with a partial opening showing the inner arrangements of elements of the instrument. Typically, the parts shown are the ones illustrated and described with reference to FIG. 2 and FIG. 12 allows to understand the inner construction and arrangement of the instrument.

The instrument according to the present invention is thus able displace needles with a simple mechanism so that after insertion, a fluid may be delivered to the body of the patient in the flesh at the desired location (compare for instance FIGS. 1 and 11).

The material used for the different parts of the instrument should be suitable for the intended (medical) use. Preferably, they should be synthetic materials, but others are possible such as metals for parts of the instrument, or a mix of materials. For example, all parts of the instrument may be made of a synthetic material and only the needles may be made of metal (such as stainless steel and other appropriate materials for the intended use).

Preferably, but not exclusively, the instrument is a "single use" instrument that is discarded after a one use.

Further, the instrument may be able to deliver a same fluid to each needle 13 or a different fluid if the channels 15 are connected to different fluid sources. Of course, the channels may be connected to a same source or to different sources, even if the same fluid (or material) is to be delivered.

The invention thus provides a medical instrument 1 comprising a tubular body 3, at least one injection needle 13 housed in said tubular body and which is movable axially, each of said at least one injection needles 13 has a radially outwardly directed tip portion, a control element in the shape of an actuator 6, said control element being rotatably controllable, said control element being in an operative connection with said at least one injection needle 13, wherein in a first axially displaced position of said control element 6 said radially outwardly directed tip portion of said needle 13 is fully housed into said instrument and in a second axially displaced portion of said control element 6 at least said tip portion of said needle 13 is positively displaced laterally out from said tubular instrument 1 by said control element 6. These measures have considerable technical advantages in terms of handling. On the one hand, it is possible to house the injection needles 13 in the body in an axially blocked manner. That is to say that these sometimes and in embodiments, the extremely thin injection needles do not have to be displaced axially (for example to extend out of the instrument), and consequently do not undergo any shearing forces. This is the case when the fluid is directly injected in the body of a patient for example. The control element 6 is designed in such a way that it is rotatably displaceable and in operative connection with the injection needle in such a way that in one position a tip portion of the needle 13 is pushed out of the instrument 1 by the control element 6, in the other position it is actively fully retracted again inside the instrument 1 (for example inside the tubular body 3) by the control element 6. This ensures that the outwardly pushed portion of the needle 13 can fully retracted again into the tubular body 1 by means of the control element 6 when the latter is rotated, so that the risk of injuries when the medical instrument is withdrawn from a cavity is eliminated completely.

The embodiments of the invention show two positions of the needles 13 or its tip (FIGS. 7-11) imposed by the two ends of the slit 4 cooperating with the locking button 5. Of course, this is only an example and the slit 4 may comprise additional stable positions for the button 5, for example a middle one, depending on the applications and if such feature is desired. Also, the embodiments described comprise four needles 13 as examples but the instrument may comprise less than four needles 13 (for example three) or more than four needles 13. Further all needles may not be the same, they may have a different size (lengths, diameter etc.) and/or shape (straight, curved etc.).

In some embodiments, high pressure injection of the fluid may be considered and allow to avoid the use of the needles 13. In such embodiments, the fluid exits the openings 20 at a sufficiently high pressure to penetrate the tissue of the patient being treated. Accordingly, the supply of fluid has to be able to provide and withstand such high pressure thereby using appropriate injection means.

The present description is neither intended nor should it be construed as being representative of the full extent and scope of the present invention. The present invention is set forth in various levels of detail herein as well as in the attached drawings and in the detailed description of the invention and no limitation as to the scope of the present invention is intended by either the inclusion or non inclusion of elements, components, etc. Additional aspects of the present invention will become more readily apparent from the detailed description above, particularly when taken together with the drawings.

Moreover, exemplary embodiments have been described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined not solely by the claims. The features illustrated or described in connection with one exemplary embodiment may be combined with the features of other embodiments. Such modifications and variations are intended to be included within the scope of the present invention. A number of problems with conventional methods and systems are noted herein and the methods and systems disclosed herein may address one or more of these problems. By describing these problems, no admission as to their knowledge in the art is intended. A person having ordinary skill in the art will appreciate that, although certain methods and systems are described herein, the scope of the present invention is not so limited. Moreover, while this invention has been described in conjunction with several embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. An instrument for a medical application, the instrument comprising:
   a body with a longitudinal axis;
   at least one needle;
   a channel fluidically connected to the at least one needle to bring a fluid to said at least one needle, the channel comprising a first part and a second part; and
   an actuator configured to move said at least one needle between a retracted position inside the body and an extended position protruding from the body, the actuator comprising a shaft, the first part of the channel extending within the shaft, the second part of the channel extending outside the shaft, a movement of the at least one needle between the retracted position and the extended position being performed by a rotation of the actuator and the shaft relative to the body,
   wherein the movement of the at least one needle between the retracted position and the extended position is rectilinear and perpendicular to the longitudinal axis,
   wherein the shaft includes a first set of teeth, and
   wherein said at least one needle includes a support having a second set of teeth cooperating with the first set of teeth.

2. The instrument according to claim 1, wherein the shaft is configured to rotate inside the body.

3. The instrument according to claim 1, wherein the first set of teeth are circularly arranged around the shaft.

4. The instrument according to claim 1, wherein the first set of teeth of the shaft and the second set of teeth of the support element have the same pitch and are configured to cooperate with each other.

5. The instrument according to claim 1, wherein the at least one needle comprises at least three needles.

6. The instrument according to claim 1, wherein the channel is flexible to flex upon a movement of said at least one needle by the actuator.

7. The instrument according to claim 1, further comprising:
   a locking device to lock a position of the actuator when the at least one needle is in the retracted position and when the at least one needle is in the extended position.

8. The instrument according to claim 1, wherein the channel and the actuator are separate elements.

9. A method of using an instrument as defined in claim 1, the method comprising the steps of:
   inserting the instrument into a cavity; and
   injecting a fluid from outside the instrument to the cavity.

10. The method as defined in claim 9, wherein the step of injecting is made through at least one opening of the instrument.

11. The method as defined in claim 9, wherein the step of injecting is performed by the at least one needle that is protruding from the instrument in the extended position.

12. The method as defined in claim 9, further comprising the step of:
   moving the at least one needle to the extended position after the step of inserting and before the step of injecting.

* * * * *